United States Patent [19]

Rapoport et al.

[11] Patent Number: 6,166,229

[45] Date of Patent: Dec. 26, 2000

[54] N-TRITYL AND N-PHENYLFLUORENYL CARBOXYANHYDRIDES OF AMINO ACIDS

[75] Inventors: Henry Rapoport, Berkeley, Calif.; Tae Bo Sim, Seoul, Rep. of Korea

[73] Assignee: The Regents of the University of California, Oakland, Calif.

[21] Appl. No.: 09/556,264

[22] Filed: Apr. 24, 2000

Related U.S. Application Data

[62] Division of application No. 09/258,469, Feb. 26, 1999, Pat. No. 6,093,831.

[51] Int. Cl.$^7$ .................................................. C07C 229/36
[52] U.S. Cl. ............................................. 552/104; 560/41

[58] Field of Search ................................. 552/104; 560/41

[56] References Cited

PUBLICATIONS

Block et al., Proceedings of the 5th European Peptide Symposium, Oxford, 1962, pp. 83–87.

*Primary Examiner*—Laura L. Stockton
*Attorney, Agent, or Firm*—Townsend and Townsend and Crew LLP

[57] ABSTRACT

Amino acids are derivatized for use in peptide synthesis by conversion to N-carboxyanhydrides that are N-protected by either a trityl or a phenylfluorenyl group.

2 Claims, No Drawings

N-TRITYL AND N-PHENYLFLUORENYL CARBOXYANHYDRIDES OF AMINO ACIDS

This application is a division of and claims thee benefit of U.S. application Ser. No. 09/258,469, filed Feb. 26, 1999, now U.S. Pat. No 6,093,831, the disclosure of which is incorporated by reference.

BACKGROUND OF THE INVENTION

A variety of methods for forming peptide bonds have been described in the literature and used in laboratories and by peptide suppliers. Included among these are the use of anhydrides of amino acids (particularly mixed carboxylic-carbonic anhydrides as well as symmetrical anhydrides of acylamino acids), the use of activated esters of amino acids (such as p-nitrophenyl esters, 3,4,5-trichlorophenyl esters, and pentafluorophenyl esters), and the use of coupling reagents (such as dicyclohexylcarbodiimide, diisopropylcarbodiimide, and carbodiimides bearing tertiary amine or quaternary ammonium groups).

Each of these methods has its own complications that limit either the yield, the reaction rate, or the economy or the efficiency of its use. A method that would appeared to avoid many of these complications is the use of N-carboxyanhydrides of amino acids as reagents. The appeal of N-carboxyanhydrides is the fact that they are easily prepared in one step with a negligible waste stream, their reactivity is high enough that they couple rapidly at room temperature with nitrogen nucleophiles, and the coupling by-product is carbon dioxide. The high reactivity however causes an inherent instability, a propensity for polymerization, and a tendency for loss of enantiomeric integrity.

Researchers have attempted to overcome these deficiencies by using an N-carboxyanhydride in which the nitrogen is additionally substituted with tosyl (p-toluenesulfonyl) (Zaoral, M., et al, *Collect. Czech. Chem. Comun.* 1961, 26, 2316) and nitrophenysulfonyl groups (Kricheldorf, H. R., Angew. Chem. 1973, 85, 86; Halstrom, J., et al., *Acta Chem. Scand., Ser. B* 1979, B33, 685), with little improvement. The most promising results were achieved recently with an alkoxycarbonyl group added to the nitrogen, forming a urethane-protected-N-carboxyanhydride (Fuller, W. D., et al, *J. Am. Chem. Soc.* 1990, 112, 7414). While this modification reduced the instability and tendency to polymerize, there still remains a significant loss of enantiomeric purity during peptide synthesis (Romoff, T. T., et al., *Peptide Res.*, 1997, 49, 281) and some instability to base.

A report of the use of N-trityl N-carboxyanhydrides in peptide synthesis appeared in 1962 (Block, H., et al., *Proceedings of the 5th European Peptide Symp.* 1962, pp. 83–87). The N-trityl N-carboxyanhydrides used in the syntheses were those of glycine and alanine. Neither of these are suitable amino acids for studying the concerns of N-carboxyanhydrides, since glycine lacks a side chain and hence an asymmetric center at its a-carbon, and alanine has a methyl group as its side chain which renders it highly stable relative to amino acids with side chains containing electron-withdrawing groups. Also, the report lacks proper confirmatory analyses of the products.

SUMMARY OF THE INVENTION

It has now been discovered that N-trityl and N-phenylfluorenyl N-carboxyanhydrides of amino acids are significantly more stable and less susceptible to polymerization than otherwise-protected N-carboxyanhydrides of amino acids, and for amino acids that have an asymmetric carbon atom center (i.e., amino acids other than glycine), the N-trityl and N-phenylfluorenyl N-carboxyanhydrides demonstrate a significant reduction or elimination of epimerization during peptide synthesis.

This invention therefore resides in the N-trityl and N-phenylfluorenyl N-carboxyanhydrides of amino acids as new compositions of matter, in methods for their preparation by the dehydration of the corresponding N-trityl and N-phenylfluorenyl amino acid, and in methods of their use in the formation of peptide bonds to prepare dipeptides, oligopeptides and polypeptides. Other objects, aspects and embodiments of the invention will become apparent from the description that follows.

DETAILED DESCRIPTION OF THE INVENTION AND PREFERRED EMBODIMENTS

While the terms "trityl" and "phenylfluorenyl" (the latter term is used herein as an abbreviation for 9-phenyl-9-fluorenyl) are well known among those skilled in the art of peptide synthesis, and used in this specification and the appended claims in the manner in which they are so known, their formulas are shown below to promote a complete understanding of the invention:

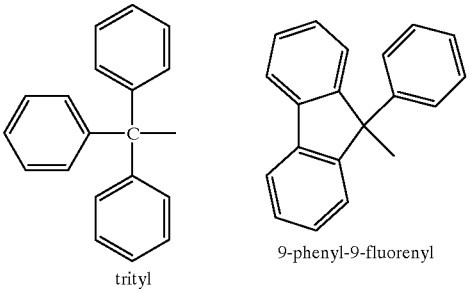

trityl   9-phenyl-9-fluorenyl

The N-carboxyanhydrides of this invention are those of the following formula

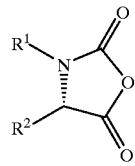

in which $R^1$ is either

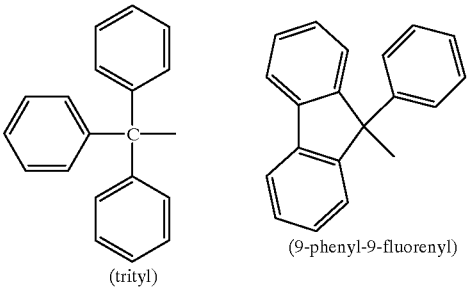

(trityl)   (9-phenyl-9-fluorenyl)

and $R^2$ is an amino acid side chain that is other than H. Again for purposes of clarity, when $R^2$ is H, the formula shown is an N-protected N-carboxyanhydride of glycine, and when $R^2$ is $CH_3$, the formula shown is an N-protected N-carboxyanhydride of alanine. The former (in which $R^2$ is H) is excluded from the scope of this invention. In preferred embodiments, the latter (in which $R^2$ is $CH_3$) is also excluded. Aside from these exclusions, the scope of $R^2$ includes any amino acid side chain, whether the side chain be that of one of the twenty common amino acids normally found in proteins, or derivatives, analogs or substituted versions of these common amino acids. Preferred amino acids are valine, isoleucine, leucine, serine, threonine, proline, aspartic acid, glutamic acid, lysine, arginine, asparagine, glutamine, cysteine, methionine, tryptophan, phenylalanine, tyrosine, and histidine.

For peptide synthesis, the N-trityl and N-phenylfluorenyl N-carboxyanhydrides of this invention are reacted with a carboxy-protected amino acid of the formula

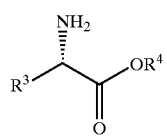

in which $R^3$ is defined as any of the groups listed for $R^2$ above plus H and $CH_3$, and $R^4$ is a carboxy-protecting group. The carboxy-protecting group may be any of the variety of groups known in the art for their ability to protect the carboxy functional group during reactions occurring at other parts of the molecule. Examples of carboxy-protecting groups are lower alkyl groups, such as methyl, ethyl, and t-butyl, benzyl groups, and p-alkoxybenzyl groups.

The reaction may be performed in a solvent, preferably a dipolar aprotic solvent. Examples of suitable solvents are dimethyl formamide, acetonitrile, dioxane, toluene, and tetrahydrofuran. Preferred solvents are dimethyl formamide and tetrahydrofuran, with tetrahydrofuran particularly preferred since the reaction can be conducted in refluxing tetrahydrofuran as a ready means of controlling the reaction temperature. The reaction can be conducted at room temperature or at elevated temperature to increase the reaction rate, although not at temperatures so high as to be detrimental to product purity. Temperatures below about 100° C. are preferred, with temperatures below about 50° C. more preferred. The reaction may be performed at atmospheric pressure.

Following the completion of the reaction, deprotection of the product at either of the protected sites can be achieved by conventional means, such as the use of dilute acids. The reaction may be performed a single time to produce a dipeptide, or a succession of times to produce oligopeptides and polypeptides, with appropriate deprotection at intermediate stages. The reaction can be used for solution peptide synthesis as well as solid-phase peptide synthesis.

This invention also resides in the discovery that catalysts that are known for use in peptide bond formation are not needed in this reaction, and in fact lower the epimeric purity of the peptide product. Thus, in further preferred embodiments of this invention, the peptide bond formation reaction is performed in the absence of catalysts, particular potassium cyanide, sodium azide and sodium fluoride.

Preparation of the N-carboxyanhydrides of the present invention is achieved with high yield and enantiomeric purity. An amino acid of the formula

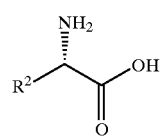

is reacted with either

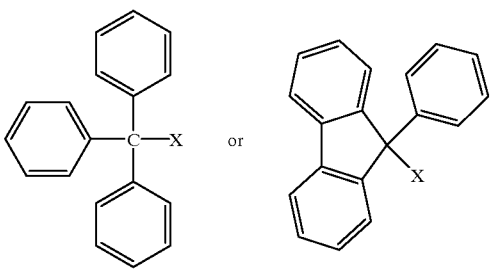

where X is a halogen atom, preferably chlorine, bromine, or fluorine, more preferably chlorine or bromine, and most preferably chlorine, in the presence of a base, to achieve as a product either an N-trityl or an N-phenylfluorenyl amino acid, and the product is then reacted with an appropriate agent to produce the anhydride. The base may be any species capable of accepting a protein from the nitrogen atom of the amino acid. One example is triethylamine; others will be readily apparent to those skilled in the art. The agent used in the formation of the anhydride may be any agent that is capable of adding a carbonyl group to an amino acid and forming the anhydride. Examples are phosgene, diphosgene, triphosgene, carbonyl diimidazole, chloroformates, and carbonates.

Both reactions are performed in a suitable inert solvent, and preferably at either ambient temperature (approximately 22° C.) or elevated temperatures under atmospheric pressure. Recovery of the product is readily achieved by conventional techniques.

The following examples are presented only as illustrations.

EXAMPLES

General procedures. Melting points were determined on a capillary apparatus and are uncorrected. Tetrahydrofuran (THF) and diethyl ether were distilled from Na-benzophenone ketyl under nitrogen; $CHCl_3$ was distilled from $P_2O_5$; dimethyl formamide (DMF) was dried over molecular sieves (3 Å) and trityl chloride was recrystallized from isooctane. Petroleum ether and hexane were used from the supplier without further purification. All final organic solutions were dried over $Na_2SO_4$ before evaporation. NMR spectra were taken in $CDCl_3$ and are referenced to tetramethylsilane. [1]H-coupling constants, J, are reported in Hz. Column chromatography was performed using 230–400 mesh silica gel. HPLC analyses were conducted on a 4.6× 250 mm–5 μm Si normal-phase silica column, monitoring at 254 nm. Elemental analyses were obtained from Microanalytical Laboratory, Department of Chemistry, University of California, Berkeley, Calif., USA 1. Synthesis of N-Triphenylmethyl (Trityl) Derivatives of L-Alanine and L-Phenylalanine

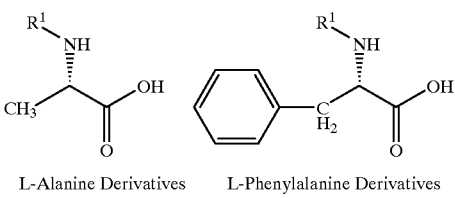

L-Alanine Derivatives   L-Phenylalanine Derivatives

To a solution of trityl chloride (30.67 g, 110 mmol) in CHCl3/DMF (350 mL, 2/1) was added the amino acid (either L-alanine or L-phenylalanine, 50 mmol) and the mixture was vigorously stirred for 3 h. Triethylamine (20.2 g, 200 mmol) in CHCl$_3$/DMF (50 mL, 2/1) was added slowly over a period of 1 h, and the mixture was stirred for another 2 h. After addition of methanol (250 mL), the reaction mixture was heated at 50–55° C. for 2 h, the solvent was evaporated, and the residue was distributed between diethyl ether (500 mL) and 10% aqueous citric acid (100 mL). The organic layer was washed with 10% aqueous citric acid (2×100 mL) and H$_2$O (3×100 mL), dried, and evaporated, and the residue was chromatographed (hexane/ethyl acetate, 6/4) to afford the N-trityl amino acid. Yields and spectral data on the products were as follows:

N-Trityl-L-alanine: 78% yield; triethylamine salt: mp 154–155° C. (literature value: 157° C.); $^1$H NMR δ 1.23 (d, J=7.1, 3H), 3.43 (q, J=7.1, 1H), 7.20–7.30 (m, 10H), 7.39–7.41 (m,5H).

N-Trityl-L-phenylalanine: eluting solvent: hexane/ethyl acetate, 7/3; 87% yield; triethylamine salt: mp 148–150° C. (literature value: 150–151° C.); $^1$H NMR δ 2.08 (dd, J=13.4, 5.8, $^1$H, 2.89 (dd, J=13.4, 6.7, 1H), 3.56 (dd, J=6.7, 5.8), 7.09–7.36 (m, 20H).

2. Synthesis of N-Trityl Derivatives of O-Benzyl-L-Serine and L-Aspartic Acid β-Methyl Ester

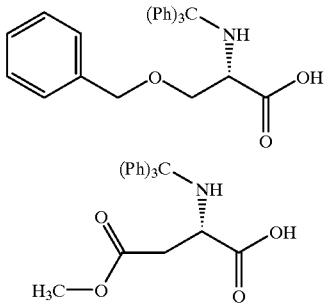

("Ph" designates phenyl.) To a solution of the amino acid (12 mmol) in CHCl$_3$/CH$_3$CN (60 mL, 5/1) was added chlorotrimethylsilane (1.52 mL, 12 mmol) and the mixture was vigorously stirred for 3 h at room temperature. Triethylamine (3.68 mL, 26.4 mmol) was then added slowly to maintain a gentle reflux, and the mixture was stirred for 15 min after which trityl chloride (4.01 g, 14.4 mmol) in 30 mL of CHCl$_3$ was added. The mixture was vigorously stirred for 3 h at room temperature; methanol (2.4 mL, 60 mmol) was added, and the mixture was stirred for an additional 30 min. The mixture was evaporated and the residue was partitioned between ether (200 mL) and aqueous 5% citric acid (60 mL). The aqueous layer was extracted with ether (2×50 mL), the combined organic solution was dried, filtered, and evaporated and the residue was chromatographed. Yields and analytical data confirming the structures of the products were as follows:

O-Benzyl-N-trityl-L-serine: eluting solvent, hexane/ethyl acetate, 8/2, then hexane/THF, 6/4; 82% yield; mp 180–181° C.; $^1$H NMR δ 2.33 (dd, J=9.1, 4.0, 1H), 3.59 (dd, J=9.1, 2.5, 1H), 3.49–3.51 (m, 1H), 4.21 (d, J=12.0, 1H), 4.32 (d, J=12.0, 1H), 7.17–7.28 (m, 20H). Elemental analysis calculated for C$_{29}$H$_{27}$NO$_3$:C, 79.6; H, 6.2; N, 3.2. Found: C, 79.7; H, 6.5; N, 3.4.

N-Trityl-L-aspartic Acid β-Methyl Ester: from L-aspartic acid β-methyl aster; after addition of trityl chloride, the reaction mixture was stirred for 5 h; eluting solvent, hexane/EtOAc, 7/3, then THF; 85% yield; mp 191–192° C.; $^1$H NMR δ 1.22 (dd, J=17.5, 5.1, 1H), 2.68 (dd, J=17.5, 3.3, 1H), 3.59 (s, 3H), 3.60–3.61 (m, 1H), 7.23–7.45 (m, 15H). Elemental analysis calculated for C$_{24}$H$_{23}$NO$_4$: C, 74.0; H, 6.0; N, 3.4. Found: C, 73.9; H, 6.2: N, 3.4.

3. Synthesis of N-(9-Phenyl-9-fluorenyl)-L-alanine

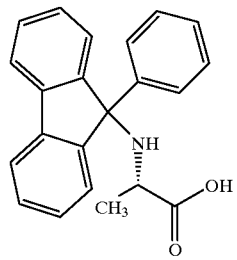

To a solution of L-alanine (4.45 g, 50 mmol) in CHCl$_3$/DMF (150 mL, 5/1) was added chlorotrimethylsilane (6.35 mL, 50 mmol) and the mixture was heated at reflux for 2 h with vigorous stirring. The mixture was cooled to room temperature under a stream of nitrogen, triethylamine (15.3 mL, 110 mmol) was slowly added to maintain a gentle reflux, and the mixture was stirred for 15 min after which Pb(NO$_3$)$_2$(10.03 g, 33.3 mmol) was added, followed by the addition of 9-bromo-9-phenylfluorene (19.3 g, 60 mmol) in 60 mL of CHCl$_3$. The mixture was vigorously stirred for 48 h at room temperature, following which methanol (5.1 mL, 125 mmol) was added. The mixture was then stirred for an additional 30 min. The mixture was then filtered, the filter cake was washed with CHCl$_3$ (3×20 mL), and the dark orange filtrate was evaporated to a residue which was partitioned between ether (300 mL) and aqueous 5% citric acid (300 mL). The aqueous layer was extracted with ether (4×100 mL) and the combined organic solution was extracted with 1 M NaOH (100 mL). The aqueous solution was washed with 100 mL of ether, cooled to 0° C. with stirring, and the pH was adjusted to 7 by the dropwise addition of glacial acetic acid. The mixture, containing an off-white precipitate, was extracted with 2-propanol/CHCl$_3$ (⅓, 5×100 mL). The combined organic solution was washed with 100 mL of brine, dried, filtered, and evaporated to a light yellow foam.

The yield and confirmation of the structure of the product by analytical data were as follows:(12.67 g, 77%): mp 153–155° C. (literature mp 158–161° C.); $^1$H NMR δ 1.00 (d, J=7.1, 3H), 2.69 (q, J=7.1, 1H), 7.07–7.40 (m, 11H), 7.64–7.70 (m, 2H).

4. Synthesis of O-Benzyl-N-(9-phenyl-9-fluorenyl)-L-serine

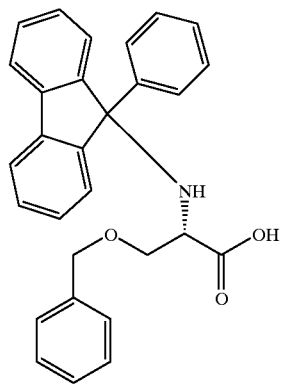

To a solution of L-serine (2.34 g, 12 mmol) in CHCl$_3$/DMF (60 mL, 5/1) was added chlorotrimethylsilane (1.52 mL, 12 mmol) and the mixture was vigorously stirred for 3 h at room temperature. Triethylamine (3.68 mL, 26.4 mmol) was then added slowly to maintain a gentle reflux, and the mixture was stirred for 15 min, after which Pb(NO$_3$)$_2$ (2.66 g, 8.0 mmol) was added, followed by the addition of 9-bromo-9-phenylfluorene (4.36 g, 14.4 mmol) in 30 mL of CHCl$_3$. The mixture was vigorously stirred for 48 h at room temperature, methanol (1.2 mL, 30 mmol) was then added, and the mixture was stirred for an additional 30 min. The resulting mixture was filtered, the filter cake was washed with CHCl$_3$ (2×50 mL), and the dark orange filtrate was evaporated to a residue which was partitioned between ether (200 mL) and aqueous 5% citric acid (60 mL). The aqueous layer was extracted with ether (2×50 mL), the combined organic solution was dried, filtered, and evaporated, and the residue was chromatographed (hexane/ethyl acetate, 8/2; hexane/THF, 6/4) to afford O-benzyl-N-(9-phenyl-9-fluorenyl)-L-serine (4.23 g, 81%) as a white solid.

The structure of the product was confirmed by analytical data as follows: mp 137–138° C.; $^1$H NMR δ 2.64–2.66 (m, 1H), 2.94 (dd, J=9.2, 4.1, 1H), 3.66 (dd, J=9.2, 2.2, 1H), 4.28 (d, J=12.0, 1H), 4.47 (d, J=12.0, 1H), 6.93–7.71 (m, 18H). Elemental analysis: calculated for C$_{29}$H$_{25}$NO$_3$: C, 80.0; H, 5.8; N, 3.2. Found: C, 79.7; H, 6.0; N, 3.1.

5. Synthesis of N-(9-Phenyl-9-fluorenyl)-L-aspartic Acid β-Methyl Ester

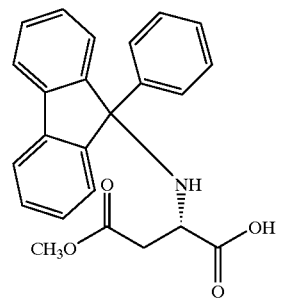

To a solution of L-aspartic acid β-methyl ester (0.44 g, 3 mmol) in CHCl$_3$/CH$_3$CN (40 mL, 3/1) was added chlorotrimethylsilane (0.38 mL, 3 mmol), and the mixture was vigorously stirred for 4 h at room temperature. Triethylamine (0.92 mL, 6.6 mmol) was added slowly to maintain a gentle reflux, and the mixture was stirred for 15 min after which Pb(NO$_3$)$_2$ (0.67 g, 2.0 mmol) was added followed by 9-bromo-9-phenylfluorene (1.16 g, 3.6 mmol) in 10 mL of CHCl$_3$. The mixture was vigorously stirred for 72 h at room temperature, methanol (0.3 mL, 7.5 mmol) was then added, and the mixture was stirred for an additional 30 min. The mixture was filtered, the filter cake was washed with CHCl$_3$ (2×20 mL), and the dark orange filtrate was evaporated to a residue which was partitioned between ether (100 mL) and 5% aqueous citric acid (50 mL). The aqueous layer was extracted with ether (2×50 mL), the combined organic solution was washed with brine (20 mL), dried, and filtered. Evaporation and chromatography of the residue (hexane/ethyl acetate, 6/4; THF) gave N-(9-phenyl-9-fluorenyl)-L-aspartic acid β-methyl ester (0.95 g, 82%) as a white solid.

The structure of the product was confirmed by analytical data as follows: mp 163–164° C. (literature mp value 160–161° C.); $^1$H NMR δ 1.95 (dd, J=17.2, 4.8, 1H), 2.76 (dd, J=17.2, 3.8, 1H), 2.86–2.88 (m, 1H), 3.65 (s, 3H), 7.22–7.76(m, 13H).

6. Syntheses of N-Trityl-and N-Phenylfluorenyl(Pf)-N-Carboxyanhydrides

Procedure A. In a first procedure for the preparation of N-trityl-N-carboxyanhydrides, by the appropriate N-trityl-amino acid (14 mmol) was added to a solution of triphosgene (1.51 g, 5.6 mmol) in ethyl acetate (280 mL). The resulting solution was treated by the dropwise addition of 1-ethylpiperidine (1.74 g, 15.4 mmol) in ethyl acetate (20 mL) over a period of 40 min, and the mixture was then stirred for another 2 h. The reaction mixture was filtered and evaporated and the residue was chromatographed through a short column (ethyl acetate). Evaporation and crystallization of the residue yielded the N-trityl-N-carboxyanhydride. Specific N-trityl-N-carboxyanhydrides prepared by this procedure, and the yields and analytical data confirming their structures, were as follows:

6.2 N-Trityl-L-alanine N-carboxyanhydride:

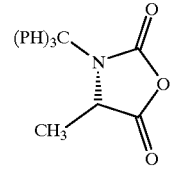

Crystallized from ethyl acetate/petroleum ether; 71% yield; 205–206° C. (literature mp value 208–210° C.); [α]$_D^{21}$+34.4° (c 0.5, ethyl acetate) [literature value [α]$_D^{21}$+34.7° (c 0.5, ethyl acetate)]; $^1$H NMR δ 0.94 (d, J=6.8, 3H), 4.51 (q, J=6.8, 1H), 7.22–7.25 (m, 5H), 7.34–7.44 (m, 10H); $^{13}$C NMR δ18.8, 57.7, 74.7, 128.0, 128.1, 129.7, 140.9, 150.9, 169.7. Elemental analysis calculated for C$_{23}$H$_{19}$NO$_3$: C, 77.3, H, 5.4; N, 3.9. Found: C, 77.2; H, 5.4; N, 3.5.

6.2 N-Trityl-L-phenylalanine N-carboxyanhydride:

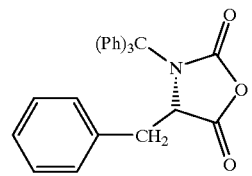

Eluting solvent: hexane/diethyl ether, 3/7; crystallized from diethyl ether/hexane; 68% yield; mp 92–95° C.; [α]$_D^{23}$+53.3° (c 1.0, ethyl acetate); $^1$H NMR 5 (dd, J=14.3, 8.3 1H), 2.88 (dd, J=14.3, 2.8, 1H), 4.46 (dd, J=8.3, 2.8, 1H), 6.84–6.85 (m, 2H), 7.20–7.37 (m, 18H); $^{13}$C NMR δ 38.0, 62.4, 75.6, 127.7, 128.1, 128.2, 128.6, 129.8, 130.0, 133.2, 140.9, 151.5, 168.4. Elemental analysis calculated for $C_{29}H_{23}NO_3$: C, 80.3, H, 5.4; N, 3.2. Found: C, 80.3; H, 5.6; N, 3.0.

Procedure B. An alternative procedure was followed in the following set of syntheses, using phosgene rather than triphosgene. According to this procedure, a solution of phosgene (0.20 g, 2.0 mmol) in benzene (0.8 mL) was added to a solution of the N-trityl or N-phenylfluorenyl amino acid (1.0 mmol) in 1,4-dioxane (26 mL). This was followed by the dropwise addition of 1-ethylpiperidine (0.453 g, 4.0 mmol) in 1,4-dioxane (4 mL), and the mixture was stirred for 3 h at room temperature. The reaction mixture was passed through a short column of $SiO_2$, with 1,4-dioxane/hexane, 7/3, and rapidly eluted with an additional 100 mL of 1,4-dioxane/hexane, 7/3. The organic solution was evaporated and the residue was recrystallized to give the N-carboxyanhydride. Specific N-trityl and N-phenylfluorenyl-N-carboxyanhydrides prepared by this procedure, and the yields and analytical data confirming their structures, were as follows:

6.3 N-Phenylfluorenyl-L-alanine N-carboxyanhydride;

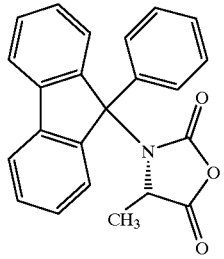

Crystallized from the THF/hexane; 81% yield; mp 107–108° C.; $[\alpha]_D^{21}$+636° (c 0.5, $CHCl_3$); $^1H$ NMR δ 0.75 (d, J=6.9, 3H), 4.40 (q, J=6.9, 1H), 7.20–7.42 (m, 9H), 7.49–7.53 (m, 1H), 7.70–7.76 (m, 2H), 7.97 (d, J=7.5, 1H); $^{13}C$ NMR δ 17.4, 57.6, 72.1, 120.2, 120.6, 124.6, 125.6, 127.1, 127.8, 128.3, 128.7, 129.1, 129.7, 129.8, 139.8, 139.9, 140.1, 143.9, 147.3, 151.3, 169.3. Elemental analysis calculated for $C_{23}H_{17}NO_3$: C, 77.7; H, 4.8; N, 3.9. Found: C, 77.5; H, 5.0; N, 4.1.

6.4 O-Benzyl-N-Phenylfluorenyl-L-serine N-Carboxyanhydride:

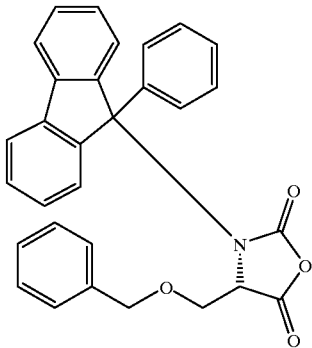

74% yield; crystallized from THF/hexane; mp 86–87° C.; $[\alpha]_D^{22}$+450° (c 1.0, $CHCl_3$); $^1H$ NMR δ 2.56 (dd J=10.2, 2.2, 1H), 3.32 (dd, J=10.2, 1.8, 1H), 3.59 (d, J+12.1, 1H), 3.71 (d, J=12.1, 1H), 4.38–4.39 (m, 1H), 6.91–6.93 (m, 2H), 7.21–7.50 (m, 13H), 7.69–7.78 (m, 2H), 7.97 (d, J=7.7, 1H); $^{13}C$ NMR δ 62.6, 66.6, 72.1, 72.6, 120.0, 120.7, 124.7, 125.8, 127.1, 127.5, 127.9, 128.2, 128.4, 128.7, 129.2, 129.6, 129.7, 136.8, 139.6, 140.4, 144.1, 146.8, 152.0, 167.4. Elemental analysis calculated for $C_{30}H_{23}NO_4$: C, 78.1; H, 5.0; N, 3.0. Found: C, 77.8; H, 5.3; N, 3.2.

6.5 O Benzyl-N-trityl-L-serine N-Carboxyanhydride:

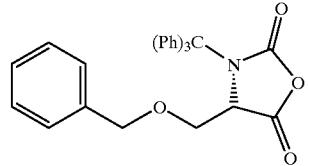

Initial eluting solvent: ethyl acetate/hexane, 1/1, followed by 1,4-dioxane/hexane, 7/3; crystallized from THF/hexane; 66% yield; mp 163–164° C.; $[\alpha]_D^{22}$+14.3° (c 15 1.5, $CHCl_3$); $^1H$ NMR δ 2.08 (dd, J=10.2, 1.2, 1H), 3.41 (dd, J=10.2, 1.2, 1H), 4.27 (d, J=11.7, 1H); 4.41 (d, J=11.7, 1H), 4.48–4.50. (m, 1H), 7.25–7.50 (m, 20H); $^{13}C$ NMR δ 62.8, 67.3, 73.5, 74.9, 127.8, 127.9, 128.0, 128.1, 125.5, 129.9, 136.5, 144.1, 151.4, 167.9. Elemental analysis calculated for $C_{30}H_{25}NO_4$: C, 77.7; H, 5.4; N, 3.0. Found: C, 77.5; H, 5.6. ; N, 2.9.

6 N-Trityl-L-aspartic Acid β-Methyl Ester N-Carboxyanhydride:

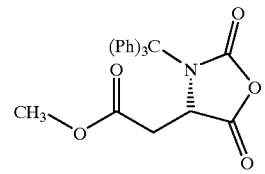

Eluting solvent: ethyl acetate/hexane, 1/1; crystallized from ethyl acetate/hexane; 71% yield; mp 156–157° C.; $[\alpha]_D^{22}$+52.8° (c 1.0, $CHCl_3$); $^1H$ NMR δ 1.56 (dd, J=17.8, 5.2, 1H), 2.54 (dd, J=17.8,2.7, 1H), 3.72 (s, 3H), 4.56 (dd, J=5.2, 2.7, 1H); 7.21–7.37 (m, 15H); $^{13}C$ NMR δ 35.3, 52.4, 58.2, 75.2, 128.1, 128.2, 129.7, 140.6, 151.7, 168.5, 169.2. Elemental analysis calculated for $C_{25}H_{21}NO_5$: C, 72.3; 14, 5.1; N, 3.4. Found: C, 72.0; H, 5.2. ; N, 3.4.

6.7 N-Phenylfluorenyl-L-aspartic Acid β-Methyl Ester N-Carboxyanhydride:

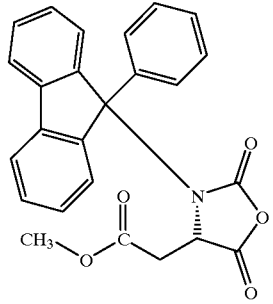

Eluting solvent: ethyl acetate/hexane, 6/4; crystallized from ethyl acetate/hexane; yield, 75%; mp 193–194° C.; $[\alpha]_D^{22}$+585° (c 1.0, $CHCl)_3$; $^1H$ NMR δ 1.69 (dd, J=18.1, 4.6, 1H), 2.48 (dd, J=18.1, 2.5, 1H), 3.23 (s, 3H), 4.49(dd, J=4.6, 2.5, 1H); 7.20–7.95 (m, 13H); $^{13}C$ NMR δ 35.8, 52.0, 57.8, 72.1, 120.4, 120.9, 124.6, 125.7, 127.9, 128.0, 128.5, 128.7, 129.1, 129.8, 130.0, 139.7, 139.8, 140.1, 143.7, 146.2, 151.8, 168.3, 168.4. Elemental analysis calculated for $C_{25}H_{19}NO_5$: C, 72.6; H, 4.6; N, 3.4. Found: C, 72.8; H, 4.7; N, 3.4.

Summarizing the results shown above, yields of the N-trityl and N-phenylfluorenyl protected amino acids ranged from 77% to 88%, and yields of the corresponding anhydrides ranged from 65% to 81%. All of the anhydrides were easily isolated, and all remained stable as crystalline compounds for several months at room temperature.

7. Formation of Dipeptides from N-Trityl- and N-Phenylfluorenyl-N-Carboxyanhydrides.

General Procedure. N-Trityl- and N-phenylfluorenyl-N-carboxyanhydrides prepared by the procedures described above were reacted with the methyl esters of amino acids to form dipeptides. Variations were made in the choice of solvent (THF in some cases, DMF in others), and in the reaction temperature (room temperature in some cases, 40° C. in others, and the reflux temperature of THF (approximately 66° C.) in still others), and catalysts (potassium cyanide, sodium azide, and sodium fluoride) were used in some cases and not in others. In all reactions, the concentration of the anhydride was approximately 0.1 M. The stoichiometry of the amino methyl ester reactant was 120 mol % relative to the anhydride. When additives were used, they were added in amounts of 100 mol % relative to the anhydride. Isolation from those reactions conducted in THF was achieved by evaporation of the solvent and chromatography of the residue. Isolation of the product from those reactions conducted in DMF was achieved by adding ethyl acetate in a volume equal to twice the reaction volume, washing with $H_2O$ (3 times, each wash equal to the reaction volume), drying and evaporating. The residue was then chromatographed and analyzed by HPLC on 5 μm silica.

The yields and analytical data for individual dipeptides prepared by this general procedure are given in the following paragraphs, where the symbol "Me" is used to designate the methyl group. The analytical data confirms the structures of the dipeptides.

7.1. N-Trityl-L-Ala-L-Phe-OMe: eluting solvent: hexane/ethyl acetate, 7/3; 81% yield; HPLC (ethyl acetate/hexane, 1/9, 2 mL/min) $t_R$ 26.6 min; mp 162–164° C.; $[\alpha]_D^{22}$ −22.1° (c 0.75, ethyl acetate); $^1H$ NMR δ 0.84 (d, J=7.1, 3H), 2.03 (d, J=5.2, 1H), 3.10 (d, J=5.7, 2H), 3.26 (dq, J=5.2,7.1, 1H), 3.72 (s, 3H), 4.56 (dt, J=5.7, 7.4, 1H), 7.10–7.11 (m, 2H), 7.18–7.36 (m, 18H), 7.69 (d, J=7.4, 1H); $^{13}C$ NMR δ 21.2, 38.0, 52.1, 52.6, 53.8, 71.9, 126.7, 217.0, 127.9, 128.5, 128.7, 129.3, 136.0, 145.5, 171.6, 175.3. Elemental analysis calculated for $C_{32}H_{32}N_2O_3$: C, 78.0; H, 6.5; N, 5.7. Found: C, 77.7; H, 6.5; N, 5.5.

7.2. N-Trityl-L-Phe-L-Ala-OMe: eluting solvent: hexane/ethyl acetate, 7/3; 72% yield; HPLC (ethyl acetate/hexane, 1/9, 2 mL/min) $t_R$ 22.4 min; mp 75–77° C.; $[\alpha]_D^{22}$ +18.3 (c 0.3, ethyl acetate); $^1H$ NMR δ 1.24 (d, J=7.2, 3H), 2.06 (dd, J=31.5, 5.5, 1H), 2.53 (d, J=6.0, 1H), 2.71 (dd, J=31.5, 5.5, 1H). 3.50 (d, J=6.0, 5.5, 5.5, 1H), 3.71 (s, 3H), 4.23 (dq, J=6.0, 7.2, 1H), 6.98–7.00 (m, 2H), 7.16–7.37 (m, 19H); $^{13}C$ NMR δ 18.6, 39.4, 47.8, 52.3, 58.7, 71.8, 126.7, 126.8, 128.0, 128.5, 128.8, 129.9, 136.6, 145.6, 173.0, 173.7. Elemental analysis calculated for $C_{32}H_{32}N_2O_3$: C, 78.0; H, 6.6; N, 5.7. Found: C, 77.8; H, 6.8; N, 5.5.

7.3. O-Benzyl-N-trityl-L-Ser-L-Phe-OMe: eluting solvent: hexane 7.5/2.5; 89% yield; HPLC (ethyl acetate/hexane, 1/9, 1.5 mL/min) $t_R$ 29.0 min; mp 47–50° C.; $[\alpha]_D^{22}$ −14.3° (c 1.0, $CHCl_3$; $^1H$ NMR δ 1.87 (dd, J=8.8,3.9, 1H), 2.91 (d, J=7.8, 1H), 3.04 (dd, J=31.7,5.7, 1H), 3.25–3.31 (m, 2H), 3.56 (dd, J=8.8, 2.1, 1H), 3.76 (s, 3H), 4.03 (d, J=11.6, 1H), 4.22 (d, J=11.6, 1H), 4.99 (ddd, J 8.7, 5.7, 4.4, 1H), 7.11–7.41 (m, 25H), 8.34 (d, J=8.7, 1H); $^{13}C$ NMR δ 38.1, 52.2, 52.5, 57.7, 69.9, 71.6, 73.2, 126.6, 127.0, 127.6, 127.7, 128.0, 128.3, 128.4, 128.5, 129.5, 135.7, 137.9, 145.8, 171.6, 172.7. Elemental analysis calculated for $C_{39}H_{38}N_2O_4$: C, 78.2; H, 6.4; N, 4.7. Found: C, 78.2; H, 6.7; N, 4.7.

7.4. N-(9-Phenyl-9-fluorenyl)-L-Ala-L-Phe-OMe: eluting solvent: hexane/ethyl acetate, 7/3; 82% yield; HPLC (ethyl acetate/hexane, 1/9, 1.5 mL/min) $t_R$ 56.6 min; mp 139° C.; $^1H$ NMR δ 1.03 (d, J=7.1, 3H), 2.21 (br s, 1H), 2.51 (q, J=7.1,1H), 3.08 (dd, J=13.7, 5.9, 1H), 3.14 (dd, J=13.7, 5.1, 1H) 3.75 (s, 3H), 4.71 (ddd, J=7.8, 5.9, 5.1, 1H), 7.02–7.48 (m, 15H), 7.61 (d, J=7.5, 1H), 7.71 (d, J=7.5, 1H), 7.96 (d, J=7.8, 1H); $^{13}C$ NMR δ 21.4, 38.1, 52.2, 52.4, 73.1, 120.0, 120.1, 124.4, 125.9, 149.2, 171.9, 174.9. Elemental analysis calculated for $C_{32}H_{30}N_2O_3$: C, 78.3; H, 6.2; N, 5.7. Found: C, 78.1; H, 6.2; N, 5.6.

7.5. O-Benzyl-N-(9-phenyl-9-fluorenyl)-L-Ser-L-Phe-OMe: eluting solvent: hexane/ethyl acetate, 7.5/2.5; 91% yield; HPLC (ethyl acetate/hexane, 1.5/8.5, 1.5 mL/min) $t_R$ 21.0 min; mp 48–50° C.; $[\alpha]_D^{22}$+175.6° (c 1.5, $CHCl_3$); $^1H$ NMR ($CHCl_3$)+1 drop of $D_2O$ δ 2.53 (dd, J=4.3, 2.5, 1H), 2.93 (dd, J=9.0, 4.3, 1H), 3.07 (dd, J=13.6, 5.7, 1H), 3.20 (dd, J=13.6, 4.4, 1H), 3.70 (dd, J=9.0, 2.5, 1H), 3.74 (s, 3H), 4.24 (d, J=11.8, 1H), 4.43 (d, J=11.8, 1H), 4.85 (ddd, J=8.8, 5.7, 4.4, 1H), 7.00–7.38 (m, 20H), 7.59 (d, J=7.5, 1H), 7.69 (d, J=7.5, 1H), 7.67 (d, J=7.5, 1H), 8.43 (d, J=8.4, 1H); $^{13}C$ NMR δ 38.1, 52.1, 52.7, 56.2, 70.1, 72.6, 73.0, 119.9, 120.0, 124.7, 125.7, 125.9, 127.0, 127.2, 127.8, 127.9, 128.0, 128.3, 128.4, 128.5, 129.6, 135.8, 137.9, 139.8, 141.1, 144.1, 147.8, 149.6, 171.6, 172.4. Elemental analysis calculated for $C_{39}H_{36}N_2O_4$: C, 78.5; H, 6.1; N, 4.7. Found: C, 78.4; H, 6.3. ; N, 4.5.

7.6. N-Trityl-β-OMe-L-Asp-L-Phe-OMe: eluting solvent: hexane/ethyl acetate, 7.5/2.5; 94% yield; HPLC (ethyl acetate/hexane, 1.5/8.5, 2.0 mL/min) $t_R$ 18.8 min.; mp 59–61° C.; $[\alpha]_D^{22}$ −28.2° (c 1.0, $CHCl_3$); $^1H$ NMR δ 0.88 (dd, J=17.5, 5.5, 1H), 2.64 (dd, J=17.5, 3.0, 1H), 3.04 (dd, J=13.7, 5.5, 1H), 3.22 (d, J=9.7, 1H), 3.32 (d, J=13.7, 4.7, 1H), 3.42 (ddd, J=9.7, 5.5, 3.0, 1H), 3.51 (s, 3H), 3.76 (s, 3H), 5.04 (ddd, J=9.2, 5.5, 4.7, 1H), 7.16–7.46 (m, 20H), 8.47 (d, J=9.2, 1H); 13C NMR δ 34.2, 38.2, 51.4, 52.2, 52.6, 54.1, 71.4, 126.7, 127.1, 128.2, 128.5, 128.8, 129.5, 135.8, 145.8, 171.6, 172.8, 172.9. Elemental analysis calculated for $C_{34}H_{34}N_2O_5$: C, 74.2; H, 6.2; N, 5.1 Found: C, 73.9; H, 6.5; N, 4.9.

7.7. N-(9-Phenyl-9-fluorenyl)-β-OMe-L-Asp-L-Phe-OMe: eluting solvent: hexane/ethyl acetate, 7.5/2.5; 92% yield; HPLC (ethyl acetate/hexane, 1.5/8.5, 20 mL/min) $t_R$ 21.0 min; mp 53–55 ° C.; $[\alpha]_D^{22}$+171° (c 1.0, $CHCl_3$); $^1H$ NMR δ 1.85 (dd, J=18.0, 5.8, 1H), 2.76–2.81 (m, 2H), 3.04 (dd, J=13.6, 5.6, 1H), 3.24 (dd, J==13.6, 4.4, 1H), 3.52 (d, J=8.7, 1H), 3.61 (s, 3H), 3.73 (s, 3H), 4.87 (ddd, J=9.0, 5.6, 4.4, 1H), 7.07–7.43 (m, 16H), 7.62 (d, J=7.5, 1H), 7.72 (d, J=7.5, 1H), 8.47 (d, J=9.2, 1H); $^{13}C$ NMR δ 35.1, 38.3, 51.6, 52.1, 52.7, 53.0, 72.6, 120.0, 120.4, 124.6, 125.5, 125.9, 127.1, 127.3, 128.0, 128.2, 128.4, 128.6, 128.7, 128.8, 129.6, 135.9, 140.8, 144.1, 147.8, 150.1, 171.6, 172.6, 172.7. Elemental analysis calculated for $C_{34}H_{32}N_2O_5$: C, 74.4; H, 5.9; N, 5.1 Found: C, 74.5; H, 6.1; N, 5.0.

7.8. N-Trityl-L-Ala-L-Phe-OMe and N-Trityl-D-Ala-L-Phe-OMe: eluting solvent: hexane/ethyl acetate, 7/3; 87% yield; HPLC (ethyl acetate/hexane, 1/9, 2 mL/min) $t_R$ 25.8 min for L, L, $t_R$ 32.8 min for D, L; $^1H$ NMR δ 0.84 (d, J=7.1), (d, J=7.0), 2.03 (d, J=5.2), 2.28 (d, J=5.8), 2.81 (dd, J=13.8, 5.7), 3.02 (dd, J=13.8, 6.1), 3.10 (d, J=5.7), 3.25–3.28 (m), 3.69 (s), 3.72 (s), 4.50–4.57 (m),7.05–7.36 (m) 7.69 (d, J=7.4).

7.9. N-Trityl-L-Phe-L-Ala-OMe and N-Trityl-D-Phe-L-Ala-OMe: eluting solvent:

hexane/ethyl acetate, 7/3; 73% yield; HPLC (ethyl acetate/hexane, 1/9, 2 mL/min) $t_R$ 22.4 min for L, L, $t_R$ 19.0 min for D, L; $^1$H NMR δ 0.99 (d, J=7.1), 1.24 (d, J=7.2), 2.06 (dd, J=13.5, 5.5), 2.53 (d, J=6.0), 2.57 (dd J=13.5, 6.6), 2.71 (dd J=13.5, 5.5), 2.80 (d, J=5.8), 2.96 (dd, J=13.5, 6.2), 3.43 (ddd, J=6.6, 6.2, 5.8), 3.50 (ddd, J=6.0, 6.5, 5.5), 3.70 (s), 3.71 (s), 4.02 (dq, J=5.8, 7.1), 4.32 (dq, J=6.0, 7.2), 6.48 (d, J=7.0), 6.98–7.37 (m).

7.10. N-(9-Phenyl-9-fluorenyl)-L-Ala-L-Phe-OMe -and N-(9-Phenyl-9-fluorenyl)-D-Ala-L-Phe-OMe: eluting solvent: hexane/ethyl acetate, 7:3; 73% yield; HPLC (ethyl acetate/hexane, 1/9, 1.5 mL/min) 55.4 min for L, L, $t_R$ 75.4 min for D, L; $^1$H NMR δ 1.03 (d, J=7.1), 1.05 (d, J=6.0), 2.20 (br s, 1H), 2.48–2.53 (m, 1H), 3.04–3.17 (m, 2H), 3.71 (s), 3.76 (s), 4.51–4.54 (m), 5.25–5.40 (ddd, J=7.8, 5.9, 5.1), 6.70–7.43 (m 15H), 7.59–7.72 (m, 2H), 7.96 (d, J=7.8, 1H).

7.11. N-Trityl-L-Ala-L-Phe-OMe and N-Trityl-D-Ala-L-Phe-OMe: eluting solvent: hexane/ethyl acetate, 7:3; 86% yield; HPLC (ethyl acetate/hexane, 1/9, 2 mL/min) $t_R$ 25.8 min for L, L, $t_R$ 32.8 min for D, L.

7.12. O-Benzyl-N-trityl-L-Ser-L-Phe-OMe and O-Benzyl-N-trityl-D-Ser-L-Phe-OMe: eluting solvent: hexane/ethyl acetate, 8/2; 86% yield; HPLC (ethyl acetate/hexane, 1/9, 1.5 mL/min) $t_R$ 25.0 min for D, L, $t_R$ 29.2 min for L,L; $^1$H NMR δ 1.87 (dd, J=8.8, 3.9), 2.26 (dd, J=9.1, 4.7), 2.90–3.34 (m, 4H), 3.48 (dd, J=9.1, 3.2), 3.56 (dd, J=8.8, 2.1), 3.66 (s), 3.76 (s), 4.03 (d, J=11.6), 4.16 (d, J=12.1), 4.22 (d, J=11.6), 4.23 (d, J=12.1), 4.69–4.74 (m), 4.99 (ddd, J=9.0, 5.7, 4.4), 7.11–7.38 (m, 24H), 7.76 (d, J=7.5), 8.34 (d, J=8.7).

7.13. N-(9-Phenyl-9-fluorenyl)-L-Ala-L-Phe-OMe, prepared in DMF in the presence of NaN$_3$, was identical with the product 7.4.

7.14. O-Benzyl-N-(9-phenyl-9-fluorenyl)-L-Ser-L-Phe-OMe and O-Benzyl-N-(9-phenyl-9-fluorenyl)-D-Ser-L-Phe-OMe: eluting solvent: hexane/ethyl acetate, 7.5/2.5; 91% yield; HPLC (ethyl acetate/hexane, 1.5/8.5, 1.5 mL/min) $t_R$ 17.8 min for D, L, $t_R$ 21.6 min for L, L; $^1$H NMR δ 2.54 (br s, 1H), 2.88 (dd, J=9.1, 4.4), 2.93 (dd, J=9.0, 4.3), 3.05–3.22 (m, 3H), 3.60–3.75 (m, 4H), 3.70 (s), 3.74 (s), 4.20 (d, J=12.1), 4.25 (d, J=11.8), 4.35 (d, J=12.1), 4.43 (d, J=11.8, 4.61–4.66 (m), 4.86 (ddd, J=8.8, 5.7, 4.4), 6.76–7.38 (m, 20H), 7.58–7.68 (m, 2H), 8.07 (d, J=8.0), 8.43 (d, J=8.4).

7.15. N-Trityl-β-OMe-L-Asp-L-Phe-OMe and N-Trityl-β-OMe-D-Asp-L-Phe-OMe: eluting solvent: hexane/ethyl acetate, 7.5/2.5; 92% yield; HPLC (ethyl acetate/hexane, 1/5, 8.5, 2.0 mL/min) $t_R$ 19.4 min for L,L; $t_R$ 27,2 min for D,L; $^1$H NMR δ 6 0.88 (dd, J=17.5, 5.5), 1.10 (dd, J=16.9, 3.2), 2.64 (d, J=17.5, 3.0), 3.04 (dd, J=13.7, 5.5), 3.18–3.32) (m), 3.30–3.35 (m), 3.39–3.44 (m), 3.51 (s), 3.52 (s), 3.75 (s), 3.76 (s), 4.75–4.80 (m), 5.04 (ddd, J=9.2, 5.5, 4.7), 7.17–7.42 (m), 8.02 (d, J=7.2), 8.47 (d, J=9.2).

7.16. N-(9-Phenyl-9-fluorenyl)-β-OMe-L-Asp-L-Phe-OMe and N-(9-Phenyl-9-fluorenyl)-β-OMe-D-Asp-L-Phe-OMe: eluting solvent: hexane/ethyl acetate, 7.5/2.5; 86% yield; HPLC (ethyl acetate/hexane, 1.5/8.5, 2.0 mL/min) $t_R$ 21.0 min for L,L; $t_R$ 31.4 min for D,L; $^1$H NMR δ 1.85 (dd, J=18.0, 5.8, 1H), 2.76–2.81 (m, 2H), 3.04 (dd, J=13.6, 5.6), 1H), 3.24 (dd, J=13.6, 4.4, 1H), 3.52 (d, J=8.7, 1H), 3.61 (s, 3H), 3.73 (s, 3H), 4.87 (ddd, J=9.0, 5.6, 4.4, 1H), 7.07–7.43 (m, 16H), 7.62 (d, J=7.5, 1H), 7.72 (d, J=7.5, 1H), 8.47 (d, J=9.2, 1H).

7.17. N-Trityl-β-OMe-L-Asp-L-Phe-OMe and N-Trityl-β-OMe-D-Asp-L-Phe-OMe: prepared in the presence of NaF, were the same as the products of 7.15, except that the ratio of diastereomers was different.

The following table summarizes the reaction conditions and results. The reaction times listed in the table were those determined for the disappearance of the anhydride as monitored by thin-layer chromatography. Abbreviations used in the table are as follows: "Trt" denotes the trityl group, "Pf" denotes the 9-phenylfluorenyl group, "Bn" denotes the benzyl group, "THF" denotes tetrahydrofuran, "DMF" denotes dimethyl formamide, and "rt" denotes room temperature (approximately 22° C.).

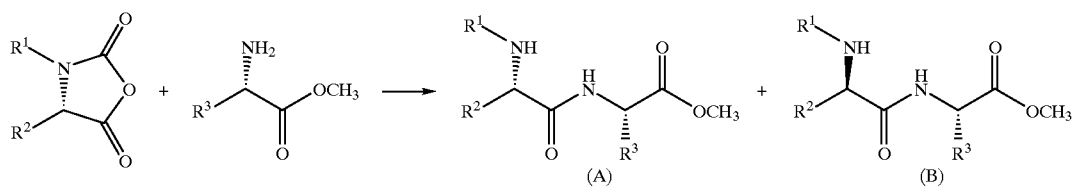

| Dipeptide No. | R$^2$ | R$^1$ | R$^3$ | Conditions: solvent/temp/time, h | Additive | Yield, % | Enantiomeric Ratio, A/B |
|---|---|---|---|---|---|---|---|
| 7.1 | CH$_3$ | Trt | Bn | THF/reflux/6 | | 81 | 100/0 |
| 7.2 | Bn | Trt | CH$_3$ | THF/reflux/7 | | 72 | 100/0 |
| 7.3 | BnOCH$_2$ | Trt | Bn | THF/40° C./20 | | 89 | 100/0 |
| 7.4 | CH$_3$ | Pf | Bn | THF/reflux/6 | | 82 | 100/0 |
| 7.5 | BnOCH$_2$ | Pf | Bn | THF/40° C./12 | | 91 | 100/0 |
| 7.6 | CH$_3$O$_2$CCH$_2$ | Trt | Bn | THF/reflux/9 | | 94 | 100/0 |
| 7.7 | CH$_3$O$_2$CCH$_2$ | Pf | Bn | THF/reflux/9 | | 92 | 100/0 |
| 7.8 | CH$_3$ | Trt | Bn | DMF/rt/3 | KCN | 87 | 36/64 |
| 7.9 | Bn | Trt | CH$_3$ | DMF/rt/3 | KCN | 73 | 23/77 |
| 7.10 | CH$_3$ | Pf | Bn | DMF/rt/3 | KCN | 73 | 87/13 |
| 7.11 | CH$_3$ | Trt | Bn | DMF/rt/3 | NaN$_3$ | 86 | 91/9 |
| 7.12 | BnOCH$_2$ | Trt | Bn | DMF/rt/15 | NaN$_3$ | 86 | 50/50 |
| 7.13 | CH$_3$ | Pf | Bn | DMF/rt/3 | NaN$_3$ | 91 | 100/0 |
| 7.14 | BnOCH$_2$ | Pf | Bn | DMF/rt/9 | NaN$_3$ | 91 | 83/17 |
| 7.15 | CH$_3$O$_2$CCH$_2$ | Trt | Bn | DMF/rt/12 | NaN$_3$ | 92 | 81/19 |
| 7.16 | CH$_3$O$_2$CCH$_2$ | Pf | Bn | DMF/rt/12 | NaN$_3$ | 86 | 98/2 |
| 7.17 | CH$_3$O$_2$CCH$_2$ | Trt | Bn | DMF/rt/15 | NaF | 88 | 97/3 |

To summarize the results of the dipeptide reactions, the two solvents performed in an equivalent manner in terms of their inertness to the reaction. The advantage of the use of tetrahydrofuran relative to dimethyl formamide is the relative ease of temperature control with tetrahydrofuran due to its low reflux temperature. The lack of catalysts in syntheses 7.1 through 7.7 did not result in a loss of yield, and with only one exception (Synthesis no. 7.13, the formation of N-(9-phenyl-9-fluorenyl)-L-Ala-L-Phe-OMe), the presence of catalysts in fact led to significant formation of the undesired enantiomer. All reactions performed in the absence of catalyst produced high yields with no formation of the enantiomer at all. It is significant to note that the epimerization took place in the N-carboxyanhydride component. This was proven by preparing authentic samples of the epimeric dipeptides by other reactions for use as controls. All reactions shown in the table resulted in dipeptides that were easily isolated, crystalline compounds. No diketopiperazine formation was detected. All of the dipeptides demonstrated complete stability for at least six months at room temperature.

The foregoing is offered for purposes of illustration. It will be readily apparent to those skilled in the art that further modifications and variations can be made without departing from the spirit and scope of the invention.

What is claimed is:

1. A process for the preparation of a dipeptide having the formula

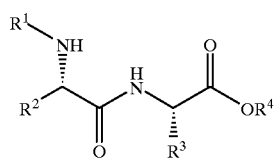

in which:

$R^1$ is a member selected from the group consisting of

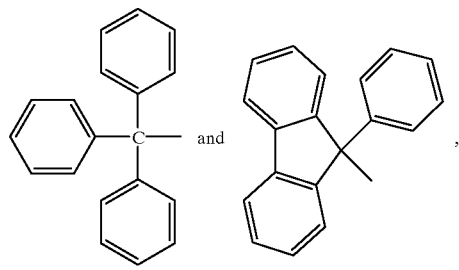

$R^2$ and $R^3$ are independently amino acid side chains with the proviso that $R^2$ is other than H and $CH_3$, and $R^4$ is a carboxy-protecting group, in a substantially epimerically pure form relative to the epimer

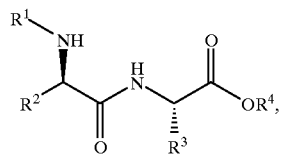

said process comprising reacting an N-carboxyanhydride of the formula

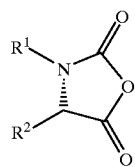

with a carboxy-protected amino acid of the formula

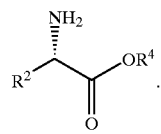

2. A process in accordance with claim 1 in which $R^2$ is a member selected from the group consisting of side chains of valine, isoleucine, leucine, serine, threonine, proline, aspartic acid, glutamic acid, lysine, arginine, asparagine, glutamine, cysteine, methionine, tryptophan, phenylalanine, tyrosine, and histidine; and $R^3$ is a member selected from the group consisting of side chains of glycine, alanine, valine, isoleucine, leucine, serine, threonine, proline, aspartic acid, glutamic acid, lysine, arginine, asparagine, glutamine, cysteine, methionine, tryptophan, phenylalanine, tyrosine, and histidine.

* * * * *